(12) United States Patent
Matsushima et al.

(10) Patent No.: US 7,682,785 B2
(45) Date of Patent: Mar. 23, 2010

(54) METHOD FOR PREDICTING EFFECTIVENESS OF CHEMOTHERAPY USING ANTICANCER AGENT

(75) Inventors: Tomoko Matsushima, Kobe (JP); Yuko Kawasaki, Kobe (JP); Hideki Ishihara, Miki (JP)

(73) Assignee: Sysmex Corporation, Hyogo (JP)

( * ) Notice: Subject to any disclaimer, the term of this patent is extended or adjusted under 35 U.S.C. 154(b) by 388 days.

(21) Appl. No.: 11/474,981

(22) Filed: Jun. 27, 2006

(65) Prior Publication Data

US 2007/0003964 A1    Jan. 4, 2007

(30) Foreign Application Priority Data

Jun. 30, 2005  (JP) .............................. 2005-190978

(51) Int. Cl.
*C12Q 1/70* (2006.01)

(52) U.S. Cl. .......................................................... 435/5

(58) Field of Classification Search ...................... 435/5
See application file for complete search history.

(56) References Cited

U.S. PATENT DOCUMENTS 6,521,407 B1   2/2003   Warenius et al.

FOREIGN PATENT DOCUMENTS

| | | | |
|---|---|---|---|
| EP | 1 600 513 A1 | 11/2005 | |
| EP | 1 686 377 A1 | 8/2006 | |
| GB | 2 334 578 A | 8/1999 | |
| JP | 2003-199585 A | 7/2003 | |
| JP | 2003-304884 A | 10/2003 | |
| WO | WO 2004/076686 A1 | 9/2004 | |
| WO | WO 2005/020794 A2 | 3/2005 | |

OTHER PUBLICATIONS

XP-002979096, "*Amplified CDK2 and cdc2 Activities in Primary Colorectal Carcinoma*", Cancer, American Cancer Society, vol. 85, No. 3, Feb. 1, 1999, pp. 546-553.

Rossi, et al, XP-002378582, "*Understanding and Modulating Cyclin-Dependent Kinase Inhibitor Specificity: Molecular Modeling and Biochemical Evaluation of Pyrazolopyrimidinones As CDK2/cyclin A and CDK4/cyclin D1 Inhibitors*", Journal of Computer-Aided Molecular Design, Escom Science Publishers BV, XX, vol. 19, No. 2, Feb. 2005, pp. 111-122.

*Primary Examiner*—Christopher H Yaen
(74) *Attorney, Agent, or Firm*—Sughrue Mion, PLLC

(57) ABSTRACT

The present invention provides a method for predicting an effectiveness of chemotherapy using an anticancer agent with high probability. The effectiveness is predicted based on a comparison of a parameter relating to CDK and/or CDK inhibitor in a tumor cell specimen obtained from a patient, with a corresponding threshold value to the parameter. The patient to be subjected this sensitivity prediction test of an anticancer agent is administered with the anticancer agent prior to removal of the tumor cell. The threshold is predetermined based on data of correlation between the selected parameter and anticancer agent therapy results obtained from a number of patients actually performed the therapy. Accordingly, the predicting method can provide information useful for determining whether to perform the chemotherapy to individual patients.

19 Claims, 3 Drawing Sheets ated pathological conditions and difference in responsiveness among cancer patients mean that some patients have to be treated with a chemotherapy using an anticancer agent which is ineffective to them, while the others receive benefits from an effective chemotherapy using an anticancer agent. Continuing administration of an anticancer agent that is not effective to a patient may only increase an adverse effect due to a side-effect, which may impose unwanted suffering to the patient.

METHOD FOR PREDICTING EFFECTIVENESS OF CHEMOTHERAPY USING ANTICANCER AGENT

TECHNICAL FIELD

This invention relates to a method for predicting an effectiveness of a chemotherapy using an anticancer agent for individual cancer patients with high probability.

BACKGROUND

Chemotherapy using an anticancer agent is known as an example of anticancer therapies. Pathological conditions of cancer patients, however, differ one from another depending on the type of the cancer, the area affected by the cancer, the stage of progression, or other factor. The versatile pathological conditions and difference in responsiveness among cancer patients mean that some patients have to be treated with a chemotherapy using an anticancer agent which is ineffective to them, while the others receive benefits from an effective chemotherapy using an anticancer agent. Continuing administration of an anticancer agent that is not effective to a patient may only increase an adverse effect due to a side-effect, which may impose unwanted suffering to the patient.

In view of the above, there is a demand for a technique of predicting, with high probability, the effectiveness of an anticancer agent for patients at an early stage of administration of the agent.

As a method for predicting the chemosensitivity of patients to an anticancer agent, Japanese Unexamined Patent Publication No. 2003-199585 (D1), for instance, discloses a method for assessing the chemosensitivity of specimen cells to an anticancer agent, wherein gene polymorphisms of BCRP contained in the specimen cells are identified based on an idea that a difference in chemosensitivity is due to the gene polymorphisms.

BCRP is an example of ABC transporters, and is known to be associated with resistance to an anticancer agent. Also, it is known that a difference in BCRP expression among the individuals is caused by single nucleotide polymorphisms (SNPs). In view of this, the chemosensitivity assessing method disclosed in D1 comprises the steps of examining the DNA sequence of cancer cells obtained from a patient; identifying a polymorphism of gene encoding BCRP; and assessing the chemosensitivity of the cancer cells to the anticancer agent or the degree of a side-effect of the anticancer agent.

Also, Japanese Unexamined Patent Publication No. 2003-304884 (D2) discloses a method comprising specifying a marker gene having compatibility to an anticancer agent with reference to the chemosensitivity of a cultured cancer cell line, and a gene expression profile of the cancer cell line in an intact state, and measuring an expression level of the corresponding to the specified marker gene in the cancer cell line of the specimen to predict compatibility of the specimen to the anticancer agent based on the obtained the expression value.

In the method disclosed in D2, if the gene group in the cancer cells of the specimen having a high relative expression amount has a high matching rate to the marker gene group having a high correlation to a certain anticancer agent, it is predicted that the specimen has compatibility to the anticancer agent. If, on the other hand, the gene group in the cancer cells in the specimen having a high relative expression amount does not show any matching to the marker gene group having a high correlation to the anticancer agent, it is predicted that the specimen does not have compatibility to the anticancer agent.

Even if the anticancer agent which is assessed to have compatibility by the above method is used for chemotherapy, it is known that the actual effectiveness of the chemotherapy is about 80%. The effectiveness of 80% is not a high rate for selecting a chemotherapy using the anticancer agent. Accordingly, an effectiveness indicator with higher probability is required for undergoing the chemotherapy in clinical facility.

There is known that p53, which is an oncosuppressor protein encoded by the p53 gene, or a retinoblastoma (RB) protein is associated with cell cycle control. In view of this, in recent years, a study has progressed concerning a relation between cancer and cell cycle related protein.

WO2004-076686 (D3) implies that a drug resistance test and prognosis are enabled by measuring at least two kinds of cell cycle related proteins and obtaining a profile of the cell cycle related proteins. D3, however, has no disclosure about a specific method or effect of the method.

SUMMARY

In view of the above, an object of the invention is to provide a method for predicting the effectiveness of a chemotherapy using an anticancer agent that enables to predict the effectiveness of the chemotherapy with high probability, and to provide a high matching rate between prediction results and actual therapeutic effects, considering individual difference among patients.

The inventors researched parameters such as activity, expression level, and the ratio of activity versus expression level of cell cycle related proteins contained in the tumor cell obtained from individuals administered with an anticancer agent, and studied the relation between the parameters and therapeutic effectiveness of the individuals actually performed the therapy using the anticancer agent, and the present invention was completed.

The present invention, therefore, provides a method for predicting an effectiveness of chemotherapy using an anticancer agent. The method comprises a comparing step (first comparing step) of comparing a parameter (first parameter) with a threshold value corresponding to the parameter, and a predicting step of predicting an effectiveness of chemotherapy using the anticancer agent on a living body based on a comparison result of the comparing step. The first parameter is selected from the group comprising (a) activity of a cyclin dependent kinase (first CDK) contained in a tumor cell, (b) expression level of said first CDK, (c) ratio of activity versus expression level of said first CDK, and (d) expression level of a cyclin dependent kinase inhibitor (CDK inhibitor) contained in the tumor cell. The tumor cell is obtained from the living body having been administered with the anticancer agent at least once.

The predicting method may further comprise a second comparing step of comparing a second parameter with a threshold value corresponding to the second parameter. The second parameter is selected from the group comprising (d) expression level of said CDK inhibitor, (e) activity of a second CDK contained in the tumor cell, (f) expression level of said second CDK, and (g) ratio of activity versus expression level of said second CDK, on condition that the selected second parameter is different from said first parameter. The second CDK is different from said first CDK. In this type method of the invention, the predicting step is carried out by predicting which class of three chemosensitivity groups the tumor cell belongs to, based on comparison results of said first and second comparing steps.

The predicting method may further comprise a third comparing step of comparing a third parameter with a threshold value corresponding to the third parameter, in addition to said first and second comparing steps. The third parameter is selected from the group comprising (a) activity of said first CDK, (b) expression level of said first CDK, (c) ratio of activity versus expression level of said first CDK, (d) expression level of said CDK inhibitor, (e) activity of said second CDK, (f) expression level of said second CDK, and (g) ratio of activity versus expression of said second CDK, on condition that the selected third parameter is different from said first and second parameters. In this type method of the invention, the predicting step is carried out by predicting which class of four chemosensitivity groups the tumor cell belongs to, based on comparison results of said first, second and third comparing steps.

In anther aspect of the present invention, one or more combinations of a comparing step and a predicting step are conducted stepwise based on achievement of the threshold value employed in the preceding predicting step. A predicting method according to this aspect comprises said first comparing step, and a first predicting step of predicting an effectiveness of chemotherapy using the anticancer agent on the living body, based on a comparison result of said first comparing step; if additional parameter is required for the prediction, the predicting method further comprises said second comparing step and a second predicting step. The second comparing step is performed after conducting the first comparing step, when a comparison result of the first comparing step is not sufficient to predict the effectiveness of chemotherapy, or when further information is required for prediction. The second predicting step is a step of predicting the effectiveness based on the comparison result of the second comparing step.

If a parameter in addition to said first and second parameters is required for predicting the effectiveness of chemotherapy, the predicting method may further comprise said third comparing step and a third predicting step. The third comparing step is performed after the second comparing step, when the comparison result of the second comparing step is not sufficient to predict the effectiveness of chemotherapy, or when further information is required for prediction. The third predicting step is a step of predicting the effectiveness based on the comparison result of the third comparing step.

In another aspect of the present invention, a combination of a comparing step and a predicting step may be conducted in a single step. According to the aspect, the predicting method comprises a first predicting step of predicting the effectiveness of chemotherapy based on a comparison of a first parameter with a first threshold value; if required for prediction, the predicting method further comprises a second predicting step of predicting the effectiveness of chemotherapy based on a comparison of a second parameter with a second threshold value; if further information is required for prediction, the predicting method further comprises a third predicting step of predicting the effectiveness of chemotherapy based on a comparison of a third parameter with a third threshold value. The first parameter is selected from the group comprising (a) activity of said first CDK, (b) expression level of said first CDK, (c) ratio of activity versus expression level of said first CDK, and (d) expression level of said CDK inhibitor. The second parameter is selected from the group comprising (a) activity of said first CDK, (b) expression level of said first CDK, (c) ratio of activity versus expression level of said first CDK, and (d) expression level of said CDK inhibitor, on condition that the selected second parameter is different from said first parameter. The third parameter is selected form the group comprising (a) activity of said first CDK, (b) expression level of said first CDK, (c) ratio of activity versus expression level of said first CDK, (d) expression level of said CDK inhibitor, (e) activity of said second CDK, (f) expression level of said second CDK, and (g) ratio of activity versus expression of said second CDK, on condition that the selected third parameter is different from said first and second parameters.

In the methods of the present invention, either one of said first CDK and said second CDK may preferably be CDK1 or CDK2. More preferably, the first CDK and the second CDK are CDK2 and CDK1 respectively. As for CDK inhibitor, p21 is preferable.

The methods of the invention are useful for predicting an effectiveness of chemotherapy using an anticancer agent sensitive against cells in M-phase. A preferable anticancer agent is a taxane.

The inventive method provides a high correlation to an effectiveness of an actual chemotherapy using an anticancer agent, and provides a superior indicator for selecting the chemotherapy. Also, with the inventive method, prediction on chemosensitivity to the anticancer agent can be made with high probability. Further, the prediction is made using tumor cells obtained from the living body having been at least once administered with the anticancer agent, which is an agent to be administered in the actual chemotherapy. Accordingly, the effectiveness of the chemotherapy can be predicted by the method, considering different responses among patients based on polymorphisms of genes encoding drug metabolizing enzymes or drug transporters.

The methods of the invention is executed by computer and provide a doctor with useful information for determining whether to perform the chemotherapy using the anticancer agent.

DETAILED DESCRIPTION OF THE PREFERRED EMBODIMENT

A predicting method of the present invention is a method for predicting an effectiveness of chemotherapy using an anticancer agent. The method comprises a comparing step of comparing a parameter relating to a cyclin dependent kinase (CDK) or a cyclin dependent kinase inhibitor (CDK inhibitor) contained in a tumor cell obtained from a living body having been administered with the anticancer agent at least once, with a threshold value corresponding to the parameter; and a predicting step of predicting an effectiveness of chemotherapy using the anticancer agent on the living body based on a comparison result of the comparing step.

The chemotherapeutic effectiveness to be predicted by the inventive method includes effectiveness by a preoperative chemotherapy and effectiveness by a postoperative chemotherapy. In the preoperative chemotherapy, it is predicted that the chemotherapy shows effectiveness if size reduction or disappearance of a primary tumor is recognized as a result of continuation of administration of an anticancer agent for patients with the primary tumor. In the postoperative chemotherapy, it is predicted that the chemotherapy shows effectiveness if a cancer relapse is not recognized for clinically unrecognizable metastasis, as a result of continuation of administration of an anticancer agent for patients who have undergone tumor extirpation. In the preoperative chemotherapy, the inventive method is effective in performing chemotherapy without a tumor extirpation, or performing a tumor extirpation after reducing the size of target tumor cells.

Tumor cell specimens to be used in the inventive method are tumor cells obtained from patients who have been administered with an anticancer agent at least once. It is preferable to use cells obtained from the patients by biopsy upon lapse of ten to thirty hours, more preferably, twenty to thirty hours after the last administration. This is because a change in activity or expression level of a cell cycle related protein by administration of an anticancer agent, which is an agent of inhibiting cell proliferation, is mostly found ten to thirty hours after the administration. Also, this period is necessary for the anticancer agent to reach the target tumor cells and invoke a change of the cell cycle.

The anticancer agent to be administered for the patients is the anticancer agent of which a chemotherapeutic effectiveness is predicted by the method of the present invention. The kind of the anticancer agent to which the method is applied is not limited as far as the anticancer agent is used for chemotherapy. If a combination of two or more anticancer agents used for chemotherapy, the combination of the two or more anticancer agents is administered in order to predict the effectiveness using the combination of the anticancer agents.

Figure 1:
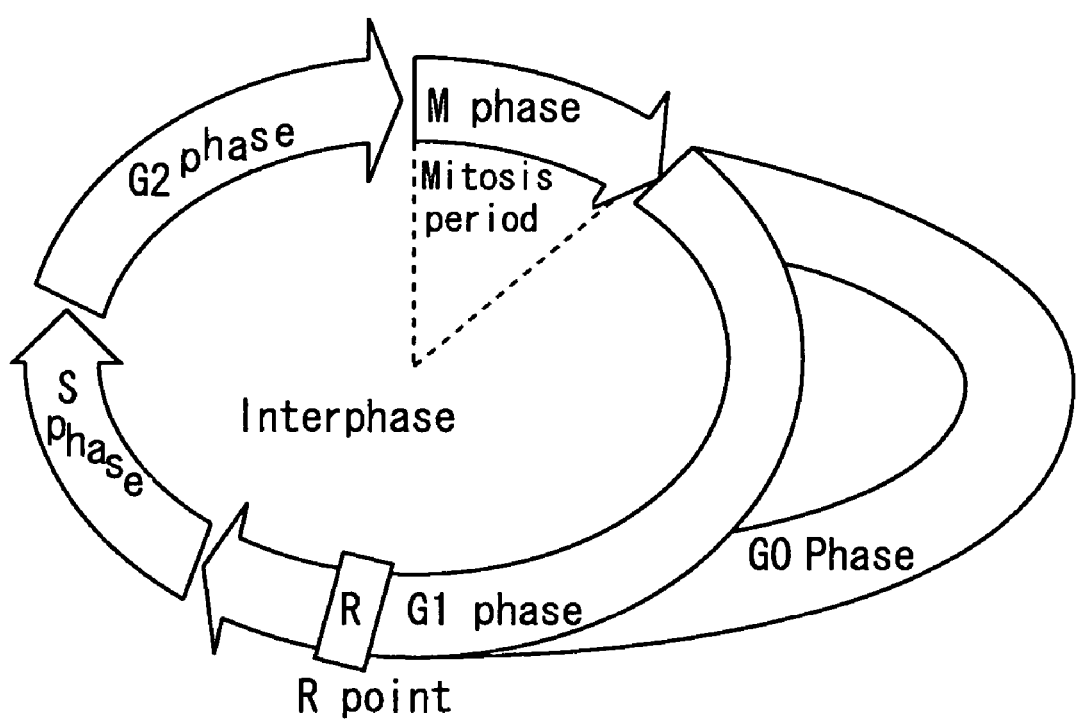
FIG. 1 is a diagram describing a cell cycle.

The cell cycle is divided into four phases: G1-phase, S-phase, G2-phase, and M-phase, as shown in FIG. 1. Referring to FIG. 1, a cell starts its proliferation, and then undergoes various events such as DNA replication, chromosome distribution, nuclear division, and cytokinesis, and returns to the starting point as two daughter cells. S-phase is a period of DNA replication. M-phase is a mitosis period. G1-phase is a period after completion of the mitosis and before start of DNA synthesis, and is a preparatory checking period before the cell enters M-phase. When the cell passes a checkpoint (in the case of an animal cell, R point) in G1-phase, the cell cycle starts, and normally the cell cycle completes without stopping at any point in the cycle. G2-phase is a period after completion of DNA synthesis and before start of mitosis. Primary checkpoints in the cell cycle are the point of time immediately before the cell enters S-phase after passing G1-phase, and the point of time when the cell directs toward mitosis after passing G2-phase. Particularly, the checkpoint in G1-phase is important because the checkpoint causes start of S-phase. After the cell passes a certain point in G1-phase, the cell cycle progresses from S-phase to G2-phase, M-phase, and then to G1-phase without stopping the proliferation, even after a proliferation signal disappears. A cell in a rest period i.e. G0-period, which is out of the cell cycle, carries the DNA content in G1-phase, and its proliferation is suspended. The cell in G0-phase can return to S-phase in the cell cycle by proliferation induction, after staying for a relatively longer time comparing with the period of G1-phase.

M-phase is a stage relating to cell division and cell proliferation. Accordingly, administering an anticancer agent that is effective against cells in M-phase enables to inhibit cell division and inhibit proliferation of tumor cells, thereby enabling to decrease the tumor cell number or cause disappearance of the tumor cells. Accordingly, a preferable anticancer agent applied in the predicting method of the invention is an anticancer agent that is effective against M-phase cells, particularly, a taxane is preferred.

A taxane anticancer agent binds to microtubules, and is conceived to accelerate polymerization and cause stabilization of the microtubules, thereby inhibiting cell division. Examples of the taxane anticancer agent are paclitaxel or docetaxel, which are anticancer agents derived from extracts of barks of Pacific yew trees or needle leaves of European yew trees.

The inventive method may predict an effectiveness of the chemotherapy using an anticancer agent to any cancer including carcinoma, sarcoma, and other malignant tumors, as far as the cancer may be treated with the anticancer agent. The kind of the cancer applied to the predicting method is not limited. Examples of the cancer include malignant lymphoma derived from hematopoietic organ such as leukemia and malignant lymphoma; carcinoma derived from epithelial cell such as breast cancer, gastric cancer, colon cancer, esophageal cancer, and prostatic cancer; and sarcoma such as osteosarcoma and soft tissue sarcoma. Examples of chemotherapy using anticancer agents for breast cancer include CMF therapy (chemotherapy using a combination of cyclophosphamide, methotrexate, and fluorouracil), chemotherapy using taxane such as docetaxel and paclitaxel, CE therapy (chemotherapy using a combination of cyclophosphamide and epirubicin), AC therapy (chemotherapy using a combination of doxorubicin and cyclophosphamide), CAF therapy (chemotherapy using a combination of fluorouracil, doxorubicin, and cyclophosphamide), FFC therapy (chemotherapy a combination of fluorouracil, epirubicin, and cyclophosphamide), chemotherapy using a combination of trastuzumab and paclitaxel, and chemotherapy using capecitabin. Examples of chemotherapy using anticancer agents for stomach cancer include FAM therapy (chemotherapy using a combination of fluorouracil, doxorubicin, and mitomycin C), FAP therapy (chemotherapy using a combination of fluorouracil, doxorubicin, and cisplatin), ECF therapy (chemotherapy using a combination of epirubicin, cisplatin, and fluorouracil), chemotherapy using a combination of mitomycin C and tegafur, chemotherapy using a combination of fluorouracil and carmustine. Examples of chemotherapy using anticancer agents for colon cancer include chemotherapy using a combination of fluorouracil and leucovorin, chemotherapy using a combination of fluorouracil and mitomycin. Examples of chemotherapy using anticancer agents for ovarian cancer include TP therapy (chemotherapy using a combination of paclitaxel and cisplatin), TJ therapy (chemotherapy using a combination of paclitaxel and carboplatin), CP therapy (chemotherapy using a combination of cyclophosphamide and cisplatin) and CJ therapy (chemotherapy using a combination of cyclophosphamide and carboplatin).

The parameter relating to CDK or CDK inhibitor is used for the prediction indicator in the inventive method. The parameter is selected from the group comprising (a) activity of a CDK contained in a tumor cell obtained from a living body, (b) expression level of the CDK, (c) ratio of activity versus expression level of the CDK, and (d) expression level of a CDK inhibitor contained in the tumor cell. The tumor cell is obtained from the living body to be subjected to the chemotherapy. The ratio of activity versus expression level may be a ratio of activity to expression level (i.e. specific activity), or a ratio of expression level to activity.

CDK is a generic term for various enzymes which are activated by binding to cycline. The CDK does not exhibit enzymatic activities by itself, but is activated by binding to cycline. The CDK acts in a specific phase of a cell cycle depending on its kind. Examples of the CDK are CDK1, CDK2, CDK4, CDK6, a cycline A-dependent kinase, a cycline B-dependent kinase, and a cycline D-dependent kinase. CDK1 and CDK2 are preferred examples.

The activity of CDK is a value which is determined based on the amount of phosphoric acid introduced into a substrate by the CDK contained in a sample to be measured, and is a value which is quantitatively calculated based on a measured value of a label (e.g. $^{32}P$, a fluorescent substance) used in measuring the phosphoric acid amount, by referring to a standard curve created in advance. The measured value is expressed by U. Specifically, there is proposed a process comprising steps of: preparing a sample containing activated CDK from a cell lysate as a specimen; labeling a substrate with $^{32}$P by reacting with $^{32}$P-labeled ATP (γ-[$^{32}$P]-ATP) on the activated CDK; measuring the amount of the labeled substrate; and quantitatively determining the phosphoric acid amount in the labeled substrate, based on a standard curve pre-created using a standard sample. Also, Japanese Unexamined Patent Publication No. 2002-335997 discloses a process without using a radioactive substance as a label. The disclosed process comprises steps of preparing a sample containing targeted activated CDK from a cell lysate as a specimen; reacting the substrate in the sample with adenosine 5'-O-(3-thiotriphosphate) (ATP-γS); introducing monothiophosphate into serine or threonine residue in the substrate; labeling the substrate by binding a fluorescent substance or a labeled enzyme to a sulfur atom in the introduced monothiophosphate; measuring the amount of the labeled thiophosphorylated substrate (or the amount of the fluorescent substance in the case where the fluorescent substance is used); and quantitatively determining the phosphoric acid amount in the specimen based on a standard curve pre-created using a standard sample.

Samples for measuring the activity of CDK are prepared by collecting target CDK from cell lysates as specimens. The preparation may be performed by using an anti-CDK antibody specific to target CDK. In the case where the activity of a specific cycline dependent kinase e.g. a cycline A-dependent kinase, a cycline B-dependent kinase, or a cycline E-dependent kinase is measured, an anti-cycline antibody specific to the cyclin depended by the kinase. In both of the case with use of the anti-CDK antibody and the case with use of the anti-cyclin antibody, the samples to be measured contain CDK other than the activated CDK. For instance, the sample may contain a CDK complex in which CDK inhibitor binds to cycline-CDK complex. Also, when the anti-CDK antibody is used, the sample may contain not only CDK itself, but also various CDK complexes such as CDK-cycline complex, CDK-CDK inhibitor complex, CDK-cyclin-CDK inhibitor complex, or complexes of CDK and other compounds. In view of this, CDK activity is measured in terms of the unit (U) of the phosphorylated substrate under the condition that various CDKs such as activated CDK, unactivated CDK, and various competitive reactive substances co-exist.

The expression level of CDK is a relative amount of target CDK (unit corresponding to the molecule number), which is contained in a cell lysate as a specimen, and can be measured by a conventional known process of measuring the amount of a target protein from a protein-containing mixture. For example, an enzyme-linked immunosorbent assay (ELISA) or a Western blot process may be used. Also, a process disclosed in Japanese Unexamined Patent Publication No. 2003-130871 may be used. A target protein i.e. CDK can be bound by using an antibody specific to the target protein. For instance, use of an anti-CDK1-antibody enables to bind CDK1s, such as CDK1 itself, CDK1-cycline complex, CDK1-CDK1 inhibitor complex, CDK1-cyclin-CDK1 inhibitor complex, and complexes of CDK1 and other compounds, in cells of the specimen.

The ratio of activity versus expression level of CDK is the ratio of CDK activity to CDK expression level i.e. specific activity of CDK, or the ratio of CDK expression level to CDK activity. The ratio corresponds to a ratio of CDK exhibiting enzymatic activities to the CDKs in the cells. The ratio can be regarded as CDK activity exhibited due to a proliferation condition inherent to tumor cells. A specimen i.e. a cell lysate, which is prepared by a specimen preparation process, particularly, prepared from tissues obtained by biopsy, is greatly affected by the amount of extracellular components, e.g. extracellular matrix contained in the tissues. However, the ratio of activity versus expression level of CDK is not influenced by the preparation process of the specimen. In view of this, the ratio of the cell lysate can be measured as a value characteristic of the tumor cell. Accordingly, the ratio of activity versus expression level of CDK is advantageous parameter in suppressing or eliminating the influence that is unavoidable in preparing the specimen. Thus, use of the ratio of CDK as a parameter in the predicting method enables to predict the effectiveness of a chemotherapy using an anticancer agent with high precision even by a protein-based method.

The CDK inhibitor represents factors that bind to cycline-CDK complexes, and inhibit the enzymatic activities thereof. The CDK inhibitor is classified into INK4 family and CIP/KIP family. In the inventive method, CIP/KIP family is preferably used, and p21 is particularly preferably used. p21 is an inhibitor which inhibits cell progression at checkpoints both in G1 phase and G2 phase in a cell proliferation cycle, and accordingly provides a time to repair damaged DNAs. In the case where the CDK inhibitor is used as a prediction indicator, the parameter of the CDK inhibitor is the expression level thereof.

The expression level of the CDK inhibitor means the amount (unit corresponding to molecule number) of a target CDK inhibitor contained in a cell lysate as a specimen, and can be measured by a conventional known process of measuring the mass of a target protein in a protein mixture. For instance, an ELISA or a Western blot process may be used. The target protein i.e. the CDK inhibitor may be bound with use of an antibody specific thereto. As far as the antibody can specifically bind to the target protein, the antibody may be a monoclonal antibody or a polyclonal antibody. In the case where p21 is employed, for instance, an anti-p21 monoclonal antibody or an anti-p21 polyclonal antibody may be used.

According to the invention, the parameter relating to CDK or CDK inhibitor is selected from the group comprising (a) activity of the CDK, (b) expression level of the CDK, (c) ratio of activity versus expression level of the CDK, and (d) expression of the CDK inhibitor. The selection of the parameter is depending on the kinds of anticancer agents or the types of cancers so that the selected parameter is suitable for predicting effectiveness of chemotherapy. The suitable parameter is determined based on analysis data about a correlation between chemotherapy results of patients having been administered with an anticancer agent and a parameter of CDK or CDK inhibitor contained in the tumor cells obtained from the patients before undergoing the chemotherapy.

In the comparing step of the method, a selected parameter is compared with a threshold value corresponding to the selected parameter. The threshold value is a value arbitrarily predetermined depending on the kinds of anticancer agents or the types of cancers. Specifically, the threshold value is a value that enables to discriminate between the effective results and non-effective results of the chemotherapy using the anticancer agent. When the parameter relating to CDK is selected, it is preferable to set the threshold value at such a value that enables to select merely the cases that all the chemotherapy results are recognized to be effective. When the parameter relating to CDK inhibitor is selected, it is preferable to set the threshold value at such a value that enables to select merely the cases that all the chemotherapy results are recognized to be non-effective. Since the threshold value is set based on actually performed clinical treatment results, the chemotherapeutic effectiveness can be predicted with high probability. The probability of effectiveness prediction can be enhanced by increasing the number of clinical treatment results. Examples of the chemotherapy results with use of anticancer agents include an observation result on a change of the tumor cell size as a result of continuation of administration of an anticancer agent, and an observation result as to whether a cancer relapse is recognized after administration of an anticancer agent for five to six years.

The predicting step of predicting an effectiveness of chemotherapy using the anticancer agent based on a comparison result of said comparing step, particularly, based on achievement of the threshold value in the comparing step. In the case where the parameter is selected from the group consisting of activity of CDK, expression level of CDK, and ratio of activity versus expression level of CDK, the predicting step is carried out by predicting whether or not the tumor cell is highly sensitive to the anticancer agent. On the other hand, in the case where the selected parameter is expression of CDK inhibitor, the predicting step is carried out by predicting whether or not the tumor cell is substantially insensitive to the anticancer agent.

According to the present invention, not only single parameter (first parameter) is selected, but also two or more parameters (i.e. a second parameter, a third parameter and so on) may be selected as a prediction indicator. In other words, one or more comparing steps may be performed in the predicting method. In each comparing step, a selected parameter is compared with a corresponding threshold value to the selected parameter.

According to the invention, a predicting method using two parameters comprises: a first comparing step of comparing a first parameter with a threshold corresponding to the first parameter; a second comparing step of comparing a second parameter with a threshold corresponding to the second parameter; and a predicting step of predicting an effectiveness of chemotherapy using an anticancer agent on the living body, based on comparison results of said first comparing step and said second comparing step.

The above-mentioned first parameter is selected from the group comprising (a) activity of a first CDK contained in a tumor cell, (b) expression level of said first CDK, (c) ratio of activity versus expression level of said first CDK, and (d) expression level of a CDK inhibitor contained in the tumor cell. The above-mentioned second parameter is selected from the group comprising (d) expression level of said CDK inhibitor, (e) activity of a second CDK contained in the tumor cell, (f) expression level of said second CDK, and (g) ratio of activity versus expression level of said second CDK, on condition that the selected second parameter is different from the selected first parameter. Accordingly, in the case where (d) expression level of CDK inhibitor is selected as the first parameter, the second parameter should be selected from the group comprising (e) activity, (f) expression level, and (g) ratio of activity versus expression level of the second CDK. On the other hand, in the case where (a) activity, (b) expression level, and (c) ratio of activity versus expression level of the first CDK is selected as a first parameter, the second parameter may be selected from the group comprising (d) expression level of said CDK inhibitor, (e) activity of the second CDK, (f) expression level of the second CDK, and (g) ratio of activity versus expression level of the second CDK. Even if the both of the first and second parameters are parameters relating to CDK, since the second CDK is different form the first CDK, the same kind or different kind of parameter from the first parameter may be selected as the second parameter. In the former case, when (a) activity of the first CDK is selected as the first parameter, for instance, the second parameter is (e) activity of the second CDK. In the later case, when (c) ratio of activity versus expression level of the first CDK is selected as the first parameter, for instance, (e) activity of the second CDK or (f) expression level of the second CDK is selected as the second parameter. When a combination of CDK inhibitor and the first or second CDK is used as a prediction indicator, any parameter can be selected for CDK.

According to the invention, when two kinds of CDK i.e. the first CDK and the second CDK are used in the predicting method, preferably, either one of the first CDK and the second CDK is CDK1 or CDK2. More preferably, the combination of the first CDK and the second CDK is a combination of CDK2 and CDK1.

In the case where two parameters are used in the method of the invention, the effectiveness of a chemotherapy using an anticancer agent can be classified into three different chemosensitivity groups e.g. high, medium, and low chemosensitivities to the anticancer agent. The different chemosensitivities to the anticancer agent are relating to different effectiveness levels of the chemotherapy: for example, a level of preventing from worsening of the patients' conditions, and a level of making the patients' conditions better by reducing the size of tumors and/or bringing disappearance of the tumors. Accordingly, the predicting step of the inventive method is carried out by predicting which class of three chemosensitivity groups the tumor cell belongs to, based on the comparison results of said first and second comparing steps.

Also, the inventive method may further comprise a third comparing step of comparing a third parameter with a threshold value corresponding to the third parameter. The third parameter is selected from the group comprising (a) activity of said first CDK, (b) expression level of said first CDK, (c) ratio of activity versus expression level of said first CDK, (d) expression level of said CDK inhibitor, (e) activity of said second CDK, (f) expression level of said second CDK, and (g) ratio of activity versus expression of said second CDK, on condition that the selected third parameter is different from said first and second parameters. In the case where (d) expression level of the CDK inhibitor is selected as the first parameter, the combination of the second parameter and the third parameter is two parameters selected from the group comprising (a) activity, (b) expression level, and (c) ratio of activity versus expression level of said first CDK, and (e) activity, (f) expression level, and (g) ratio of activity versus expression level of said second CDK. When both of the second parameter and the third parameter are parameters of the same CDK (e.g. second CDK), different kinds of parameters should be selected each other. For instance, when both of the second parameter and the third parameter are parameters relating to the second CDK, two parameters are selected from the group comprising activity, expression level, and ratio of activity versus expression level for the second and third parameters. Examples of the combination of the second and third parameters include a combination of (e) and (f), a combination of (e) and (g), and a combination of (f) and (g). When two kinds of CDK (i.e. both of first CDK and second CDK) are employed for the second and third parameters, any kind of parameters may be selected from the group comprising activity, expression level, and ratio of activity versus expression level as the second and third parameters respectively. As far as the kind of CDK is different each other, both of cases, that is, the case that the kind of parameters for the second and third parameters is identical to each other, and the case that the kind of parameter for the second parameter is different from the third parameter, can be employed. In the former case, when (f) expression level of the second CDK is used as the second parameter, for instance, (b) expression level of the first CDK is used as the third parameter. In the later case, when (f) expression level of the second CDK is used as the second parameter, for instance, (a) activity of the first CDK or (c) ratio of activity versus expression level of the first CDK may be used as the third parameter.

In a word, as far as either one of the kind of protein (i.e. the first CDK, the second CDK, or the CDK inhibitor) to be used for the parameter or the kind of parameter (i.e. activity, expression level, or ratio of expression level versus activity) is different one from another among the first, second, and third parameters, any parameter can be selected in the comparing steps.

In the case where three comparing steps using three parameters are carried out, the effectiveness of a chemotherapy using an anticancer agent can be classified into four groups by the degree of the chemotherapeutic effectiveness e.g. high, medium, slightly low, and low chemosensitivities to the anticancer agent, based on the comparison results of the first, second, and third comparing steps. That is, the predicting step is carried out by predicting which classes of four chemosensitivity groups the tumor cell belongs to, based on the comparison results of the first, second, and third comparing steps.

Accordingly, the inventive predicting method comprising two or more comparing steps (e.g. second comparing step, third comparing steps and so on) is advantageous in raising the correct probability in prediction.

According to the invention, in the case where two or more parameters, e.g. a first, second, and third parameters are used in the predicting method, the respective comparing steps for the first to third parameters may be carried out in such a manner that the succeeding comparing step is performed based on the comparison result of the preceding comparing step. Whether the succeeding comparing step is performed is depending on the comparison result of the previous comparing step. This type predicting method can be called as "stepwise predicting method", when required to discriminate from the predicting method needed to conduct all comparing steps independently each other.

According to the stepwise predicting method, a predicting method comprises a first comparing step of comparing said first parameter with said first threshold value, and a first predicting step of predicting the effectiveness of chemotherapy based on a comparison result of the first comparing step. If required for predicting the effectiveness, the predicting method further comprises a second comparing step of comparing said second parameter with said second threshold value, and a second predicting step of predicting the effectiveness of chemotherapy based on a comparison result of the second comparing step. The second comparing step is performed when a comparison result of the first comparing step is not sufficient to predict an effectiveness of chemotherapy on the living body or when further information is required for prediction. For instance, when expression level of CDK inhibitor as the first parameter is smaller than the threshold value, the obtained prediction result for the anticancer agent would not be insensitive to the tumor cell. Thus, this prediction is not sufficient and further information is required for determining whether to perform a chemotherapy using the anticancer agent. Also, for instance, when the first comparing step is carried out by comparing a first parameter relating to the first CDK with a first threshold value, the first predicting step is carried out by predicting the effectiveness of chemotherapy based on achievement of the first threshold value. In case that the first parameter does not exceed the first threshold value, the second comparing step and the second predicting step further carried out may provide more useful prediction, as comparing with a single prediction given by the first predicting step.

In the above-mentioned stepwise predicting method, the second parameter may be selected in the same manner as a predicting method in which two comparing steps are performed independently each other. However, in the stepwise predicting method, there is a case where the second comparing step is unnecessary to carry out. For instance, in case that the first parameter relating to CDK is achieved the first threshold, the second comparing step and the second predicting step may not be carried out.

According to the invention, a stepwise predicting method performing the first to third comparing steps in order comprises a first comparing step of comparing said first parameter with a first threshold value, and a first predicting step of predicting the effectiveness of a chemotherapy based on a comparison result of said first comparing step; if required, the predicting method further comprises a second comparing step of comparing said second parameter with a second threshold value, and a second predicting step of predicting the effectiveness of chemotherapy based on a comparison result of the second comparing step; if required, the predicting method further comprises a third comparing step of comparing said third parameter with a third threshold value, and a third predicting step of predicting the effectiveness of chemotherapy based on a comparison result of the third comparing step. As described above, the second comparing step is performed after the first comparing step when a comparison result of the first comparing step is not sufficient to predict the effectiveness or when further information is required for determining whether to perform a chemotherapy using the anticancer agent. And the third comparing step is performed after the second comparing step when a comparison result of the second comparing step is not sufficient to predict the effectiveness or when further information is required for determining whether to perform the chemotherapy using the anticancer agent. According to this stepwise predicting method, prediction is based on the first predicting step; if the second predicting step is performed, the prediction is based on the second predicting step; and if the third predicting step is performed, the prediction is based on the third predicting step.

In this stepwise predicting method, the third parameter is selected from the group comprising (a) activity of said first CDK, (b) expression level of said first CDK, (c) ratio of activity versus expression level of said first CDK, (d) expression level of said CDK inhibitor, (e) activity of said second CDK, (f) expression level of said second CDK, and (g) ratio of activity versus expression of said second CDK, on condition that the selected third parameter is different from said first and second parameters. The selection of the third parameter is made in the same manner as the method in which all of three comparing steps are performed independently each other. According to the invention, preferably, the first parameter is the ratio of activity versus expression level of said first CDK, the second parameter is the expression level of said CDK inhibitor, and the third parameter is the ratio of activity versus expression level of said second CDK. Furthermore preferably, the first CDK is CDK2 and the second CDK is CDK1.

Therefore, a preferable embodiment of the stepwise predicting method comprises a first comparing step of a comparing a first parameter relating to said first CDK with a first threshold value, and a first predicting step of predicting the effectiveness of a chemotherapy based on achievement of the first threshold value; in case that the first parameter does not exceed the first threshold value, the method further comprises a second comparing step of comparing a second parameter relating to said CDK inhibitor with a second threshold, and a second predicting step of predicting the effectiveness of chemotherapy based on achievement of the second threshold value.

According to the stepwise predicting method of the invention, a comparing step and a predicting step may be conducted in a single step. Therefore, another embodiment of the stepwise predicting method comprises a first predicting step of predicting the effectiveness of chemotherapy based on a comparison of said first parameter with a first threshold value; if required, the method further comprises a second predicting step of predicting the effectiveness of chemotherapy based on a comparison of said second parameter with a second threshold value; if required, the method further comprises a third predicting step the effectiveness of chemotherapy based on a comparison of said third parameter with a third threshold value. A preferable embodiment of this type stepwise predicting method comprises a first predicting step of predicting the effectiveness of chemotherapy based on a comparison of said first parameter relating to said first CDK, with a first threshold value; in case that the first parameter does not exceed the first threshold value, the method further comprises a second predicting step of predicting the effectiveness of chemotherapy based on a comparison of said second parameter relating to CDK inhibitor with a second threshold value; in case that the second parameter does not exceed the second threshold value, the method further comprises a third predicting step of predicting the effectiveness of chemotherapy based on a comparison of said third parameter relating to said second CDK with a third threshold value.

The stepwise predicting method can provide the same prediction result as the result predicted by the method in which all comparing steps are performed independently each other. That is, the chemotherapeutic effectiveness predicted by the method is based on the classified chemosensitivity groups: e.g. high, medium, and low. As described above, if an intended prediction result can be obtained in the course of the process in the stepwise predicting methods, there is no need of performing a succeeding comparing step and predicting step. Accordingly, the stepwise prediction method can make the prediction process simple, comparing with the predicting method in which all comparing steps are performed independently each other.

Figure 2:
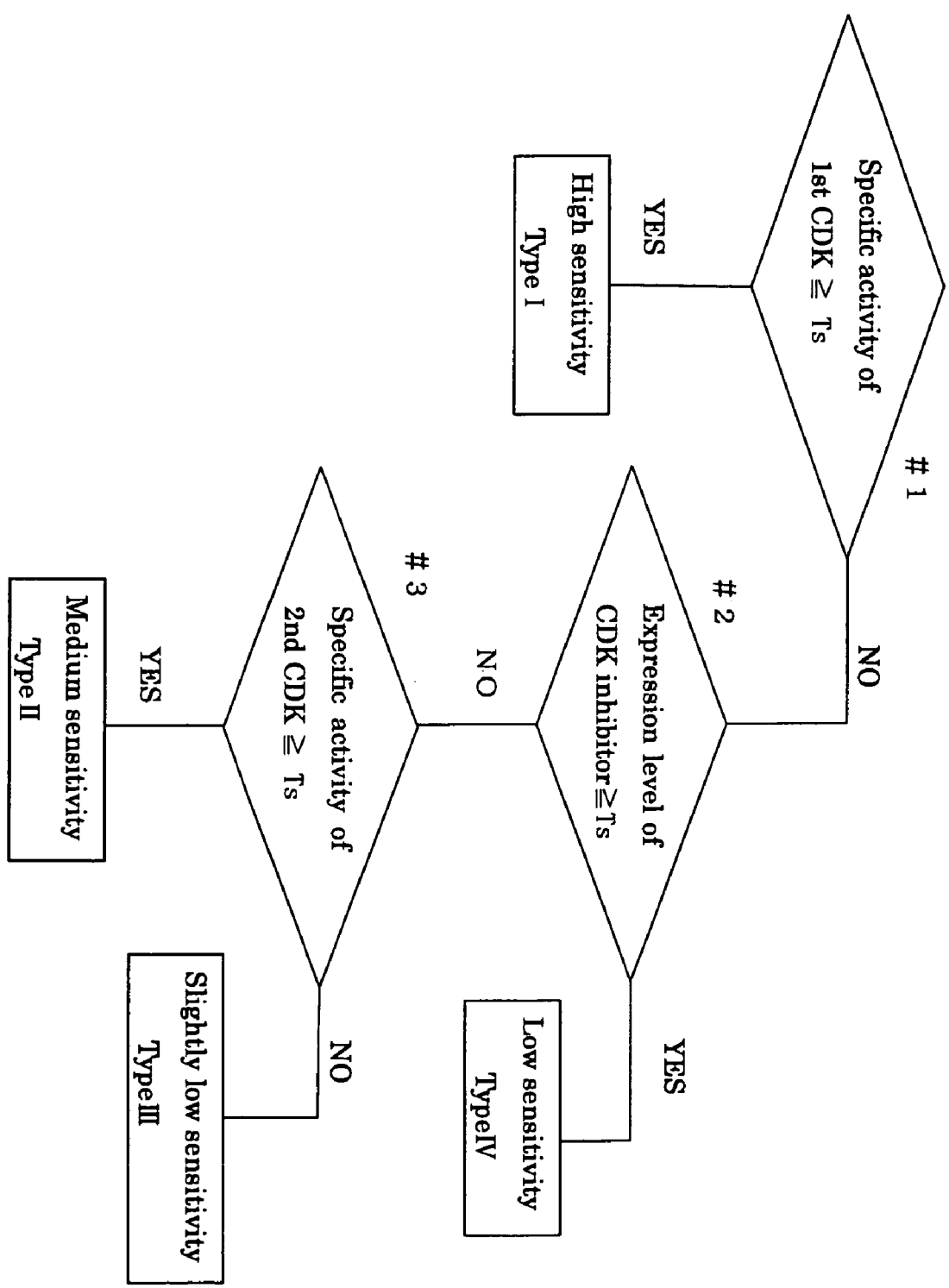
FIG. 2 is a flowchart showing operations of prediction according to a predicting method embodying the invention.

An example of the prediction method wherein three comparing steps are performed in order is described referring to a decision tree flowchart shown in FIG. 2

First, a specific activity of the first CDK in a specimen cell is compared with a predetermined threshold value (Ts) thereof (Step #1). If the specific activity is higher than the threshold value (YES in Step #1), it is predicted that the specimen cell has a high chemosensitivity to the administered anticancer agent. In this case, it is predicted that the chemotherapeutic effectiveness of the anticancer agent is high. Accordingly, in the clinical facility, the decision for selecting chemotherapy may be made.

If, on the other hand, the specific activity is not higher than the threshold value (NO in Step #1), the expression level of the CDK inhibitor is compared with a predetermined threshold value (Ts) thereof (Step #2). If the expression level is higher than the threshold value (YES in Step #2), it is predicted that the specimen cell has a low chemosensitivity. In this case, it is predicted that the chemotherapeutic effectiveness of the anticancer agent is low. Accordingly, in the clinical facility, the administration of the anticancer agent can be stopped, which enables to reduce physical load to the patient who is predicted to show a low chemotherapeutic effectiveness to the anticancer agent due to a side-effect, as well as reduction of economic burden.

If, on the other hand, the expression level is not higher than the threshold value (NO in Step #2), the specific activity of the second CDK in the specimen cell is compared with a predetermined threshold value (Ts) thereof (Step #3). If it is judged that the expression level of the second CDK is higher than the threshold value (YES in Step #3), it is predicted that the specimen cell has a medium chemosensitivity. If, on the other hand, the specific activity is not higher than the threshold value (NO in Step #3), it is predicted that the specimen cell has a slightly low chemosensitivity.

In the decision tree flowchart shown in FIG. 2, the combination of the first CDK and the second CDK is arbitrarily selected depending on the kind of the anticancer agent to be administered. If the anticancer agent is a taxane anticancer agent, combination of CDK1 and CDK2 is preferred, more preferably, the first CDK and the second CDK are CDK2 and CDK1 respectively. Also, it is preferred to use p21 as the CDK inhibitor.

According to the decision tree mentioned above, the chemosensitivity of the patient to the anticancer agent can be predicted by four grades, i.e. high chemosensitivity corresponding to type I, medium chemosensitivity corresponding to type II, slightly low chemosensitivity corresponding to type III, and low chemosensitivity corresponding to type IV. Further, if the specimen cell is predicted to have a high chemosensitivity in the Step #1, the succeeding comparing step is not made for the specimen cell, which simplifies the prediction process.

Although the comparisons of the first CDK, the second CDK, and the CDK inhibitor with the corresponding respective threshold values are made in this order in the embodiment shown in FIG. 2, the comparison order may be arbitrarily changed, according to the invention.

In the inventive method, parameters as the prediction indicator is prepared by measuring activity and expression level of CDK and/or CDK inhibitor with use of the tumor cell having been administered with the anticancer agent at least once for chemosensitivity prediction test. Accordingly, chemosensitivity to the anticancer agent may be predicted, considering not only chemosensitivity to the anticancer agent depending on the kind of tumor cells, but also individual differences among patients concerning chemosensitivity such as metabolic activity against the agent, which is conclusively observed as differences in activity and/or amount of CDK or CDK inhibitor. The difference may be related to differences in chemotherapeutic effectiveness among the patients. Thus, the inventive method may provide high-precision prediction results, considering pharmacokinetic differences among individuals depending on polymorphisms of genes encoding drug metabolizing enzymes or drug transporters.

According to the invention, the inventive method may be executed by a computer as a computer program. The program may be recorded on a medium. Also the program may be a download file.

The above-mentioned measurement of activity and/or expression level of CDK and/or CDK inhibitor and the above-mentioned prediction may be conducted automatically by a machine and so on.

EXAMPLES

First, measurement methods used in the following examples are described.

[Measurement Method]

(1) Measurement of CDK Activity

A tissue specimen containing target tumor cells was prepared in a 1.5 ml-Eppendorf tube so that 100 μg lysate in terms of total protein mass was dissolved in a buffer solution of 500 μl. To the buffer solution, added were sepharose beads (Bio-Rad, Calif., U.S.A.) coated with 20 μl of a protein A and 2 μg of antibodies specific to the CDK whose activity was to be measured, i.e. polyclonal anti-CDK1-antibodies or polyclonal anti-CDK2-antibodies (Santa Cruz Biotechnology, Santa Cruz, Calif.). After the addition, the solution was reacted at 4° C. for 1 hour. Thereafter, the beads were washed with a buffer solution (0.1% NP-40 and 50 mM tris-HCl adjusted pH 7.0) three times, followed by re-suspension in a kinase buffer of 15 μl. Thus, a sample containing the beads to which the target CDK binds was yielded.

In the sample, all the CDK (hereinafter, if distinction is not necessary, simply called as "CDKs") including CDK itself, activated CDK to which cycline binds, complexes of activated CDK and CDK inhibitor, and complexes of CDK and CDK inhibitor were bound to the antibodies, thereby fixing the CDKs to the beads. The activity of the CDKs in the sample was measured by the following measurement method.

Prepared was a substrate solution containing 5 mM adenosine 5'-O-(8-thiotriphosphate) (ATP-γS (Sigma)), a buffer solution (20 mM tris-HCl (pH: 7.4), 0.1% Triton-X-100), and 10 μg histon H1 (Upstate Biotechnology, Lake Placid, N.Y.) as a substrate for CDK1 and CDK2. The substrate solution was added to the aforementioned sample solution containing the CDKs up to the total volume of 50 μl. The resulting sample solution was shaken for 10 minutes at 37° C. for incubation. As shown by the following formula, serine or threonine residue in the substrate was phosphorylated by the activated CDK, and monothiophosphorylated substrate was yielded.

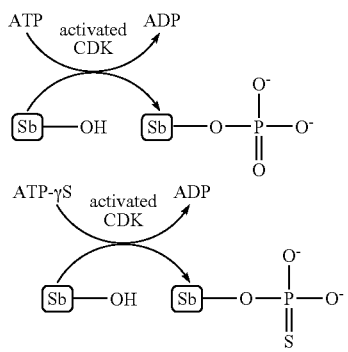

After the reaction, the sample solution was centrifuged at 20,000 rpm for 20 seconds to precipitate the beads, and 18 μl of a supernatant in which monothiophosphates were dissolved was obtained. To 18 μl of the supernatant, added was 15 μl of a buffer solution (150 mM tris-HCl (pH: 9.2) and 5 mM EDTA). Further, the resultant solution was incubated in 10 mM iodoacetyl biotin solution (100 mM tris-HCl (pH: 7.5) and 1 mM EDTA) in a dark place for 90 minutes at room temperature. Thereby, sulfur ions in the thiophosphates in the monothiophosphorylated substrate were labeled by biotinylation. The reaction of the iodoacetyl biotin with the thiophosphates was stopped by adding 6-mercaptoethanol.

0.4 μg of the biotinylated thiophosphorylated substrate was blotted on a PVDF membrane by using a slot blotter for adsorption. The blotted membrane was blocked with 1% of bovine serum albumin (BSA) for 30 minutes, followed by reaction with avidin-FITC (Vector, Burlingame, Calif.) at 37° C. for 1 hour. Thereafter, the membrane was washed with 50 mM TBS (25 mM tris-HCl (pH: 7.4) and 150 mM NaCl) for 10 minutes three times. After the washing, the image on the membrane was analyzed by a fluorescent image analyzer (Bio-Rad, Calif. U.S.A.). The activity of the CDKs was calculated based on a standard curve.

The standard curve was created by adsorbing a protein (biotinylated immunoglobulin) of a known amount to a PVDF membrane, labeling the protein with FITC in the same manner as mentioned above, and measuring the fluorescent intensity of the protein by the fluorescent image analyzer (Bio-Rad). 1 U of the CDK activity to be measured is a value representing the fluorescent intensity substantially equivalent to the fluorescent amount of the target protein of 1 ng.

(2) Measurement of Expression Level of CDK

An initialized PVDF membrane (Millipore, Billerica, Mass.) obtained by immersing the membrane in TBS (25 mM tris-HCl (pH: 7.4) and 150 mM NaCl) was set to a well plate for slot blotter. Into each well (2×2×3 mm, allowable content: 100 μl) of the well-plate, 50 μl each of the tissue specimens (cell lysate of the target tumor cells) was seeded, and samples for measuring the expression level of CDK were prepared. The sample in each well contains the protein in the total amount of 5 to 15 μg.

After seeding the samples in the wells, the samples were adsorbed onto the membrane by applying a negative pressure of about 200 mmHg from the bottom of the wells i.e. the backside of the membrane for about 50 seconds.

Then, a solution containing rabbit anti-CDK1-antibodies or rabbit anti-CDK2-antibodies, which is primary antibody being able to bind to the samples specifically, was seeded into each well, and the well plate was placed stationary at room temperature for about 30 minutes. Thereafter, the samples were adsorbed onto the membrane from the bottom of the wells with a negative pressure of 500 mmHg for about 50 seconds. Then, the membrane was washed with TBS (25 mM tris-HCl (pH: 7.4) and 150 mM NaCl).

Subsequently, a solution containing biotinylated anti-rabbit-antibodies (secondary antibody) was seeded into each well, and the well plate was placed stationary at room temperature for about 30 minutes. Then, the samples in the wells were adsorbed onto the membrane from the bottom of the wells with a negative pressure of 500 mmHg for about 50 seconds. Thereafter, the membrane was washed with TBS (25 mM tris-HCl (pH: 7.4) and 150 mM NaCl).

Then, 40 μl each of an FITC-labeled streptavidin reagent was seeded into the wells, and the well plate was placed stationary at room temperature for about 30 minutes to label the secondary antibody with the FITC. After the labeling, the samples were adsorbed onto the membrane with a negative pressure of 500 mmHg for about 50 seconds. Thereafter, the membrane was washed with TBS (25 mM tris-HCl (pH: 7.4) and 150 mM NaCl).

After the PVDF membrane was removed from the well plate, the membrane was washed with distilled water, dried for about 15 minutes at room temperature. Thereafter, the fluorescent intensity of the protein adsorbed to the membrane was analyzed and measured by the image analyzer (Bio-Rad). The FIFC-labeled protein (CDK1 or CDK2) was quantified based on the previously created standard curve by converting the amount corresponding to the amount of CDK into the weight (ng) of the standard protein. The amount of CDKs measured by the above process is the total amount of the CDKs in the cells, such as CDK itself and CDK complexes (CDK-cycline complex, CDK-cyclin-CDK inhibitor complex, CDK-CDK inhibitor complex, and complexes of CDK and other compounds).

The standard curve was created by seeding 50 μl each of solutions containing a purified recombinant CDK protein in five different concentrations in TBS containing 0.001% NP-40 and 50 μg/ml BSA into the wells which have been processed in the similar manner as mentioned above, labeling the protein with the FITC according to the similar manner as mentioned above, measuring the fluorescent intensity of the labeled protein, and expressing a relation between the fluorescent intensity of the labeled protein, and the amount of the CDK protein.

(3) Calculation on Specific Activity of CDK

The specific activity (mU/ng) of CDK was calculated based on the measured CDK activity and the measured expression level of CDK in accordance with the following equation.

$$\text{CDK specific activity} = \text{CDK activity}/\text{CDK expression level}$$

(4) Measurement of Expression Level of p21

Expression level of p21 is measured using CALIBIOCHEM p21 WAF 1 ELISA kit (EMD Bioscience Inc.).

WAF1 sample solutions (mixture solutions of specimen and WAF1 standard solution containing lyophilized WAF1) were prepared by diluting the WAF1 standard solution (20 unit/ml lyophilized WAF1) stepwise with the cell lysate as the specimen. In each of the sample solutions, the cell lysate was diluted 4-times or more.

Into 96-well plastic plate in which rabbit polyclonal antibodies (primary antibody) specific to WAF1 was coated, 100 μl each of the WAF1 sample solution and the WAF1 standard solution were individually seeded into the wells. The well plate was sealed and incubated at room temperature for 2 hours for reaction with the primary antibody.

After the well plate was washed with a cleaning buffer, which was prepared by adding 25 ml of a 20-times concentrated solution to 475 ml de-ionized water, three times, 100 μl of antibodies (biotinylated anti-WAF1 monoclonal antibodies) for detection of CDK were added to each well. Thereafter, the well plate was sealed and allowed to react at room temperature for 1 hour.

After the reaction, the well plate was washed with the cleaning buffer three times, and then, 100 μl of a peroxidase-conjugated streptavidine diluent was added into each well, and the mixture was stirred moderately. Thereafter, the well plate was sealed and allowed to react at room temperature for 30 minutes. After reaction, unbound peroxidase-conjugated streptavidine was removed by washing with the cleaning buffer three times. And then, 100 μl of a substrate solution (pigment source substrate) was added into each well, and the mixture was reacted at room temperature for 30 minutes. Upon lapse of 30 minutes after the addition, 100 μl of a stop solution (2.5 N sulfuric acid) was poured into each well to stop the reaction. Then, absorbance of each well's contents was measured using a plate reader at dual wavelength of 450/540 nm.

The concentration of p21WAF1 in the WAF1 sample solutions was calculated based on a standard curve of the WAF1 standard solution.

Example 1

Relation between Chemotherapeutic Effectiveness and Prediction using Mouse Heterograft (1) Preparation of Specimen 5 kinds of human-derived breast cancer cultured cells (cells A to E) were subcutaneously implanted on the backs of forty-six mice (No. 1 to 46). The mice were raised for 21 to 28 days to engraft the breast cancer cells. The cancerous mice No. 1 to 46 were administered with paclitaxel of 20 mg/kg with respect to the weight of each mouse. Upon lapse of 24 hours after the administration, tissues (about 50 mg) in the size of 2.5 mm×2.5 mm was cut from the back of each mouse. Each of the tissues were homogenized using an electric homogenizer to dissolve dissolvable components in a buffer solution containing 0.1 w/v % nonidet P-40 (NP-40) (Calbiochem), 50 mM tris-HCl (pH: 7.4), 5 mM EDTA, 50 mM sodium fluoride, 1 mM sodium orothovanadate, and 100 μl/ml of protease inhibitor cocktail (Sigma, St. Louis, Mo.).

After removing insoluble components by centrifuging at 15,000 rpm for 5 minutes at 4° C., the obtained supernatants (cell lysates) were used as specimens.

(2) Effect of Anticancer Agent Therapy for Cancerous Mice

Each of cancerous mice No. 1 to 46, which was produced in the experiment (1) and bore any one of cells A to E, was administered with paclitaxel of 20 mg/kg with respect to the weight of each mouse once a day for 5 days. The tumor size was measured from the start of the administration to the 11th day after the start of the administration. The chemotherapeutic effectiveness was classified, according to the change in tumor size, into Type I (high chemosensitivity), Type II (medium chemosensitivity), Type III (slightly low chemosensitivity), and Type IV (low chemosensitivity). Type I means that chemosensitivity to the anticancer agent was high, wherein the tumor almost completely disappeared by administration of paclitaxel. Type II means that chemosensitivity to the anticancer agent was medium, wherein the tumor size was reduced by administration of paclitaxel. Type III means that chemosensitivity to the anticancer agent was slightly low, wherein increase of the tumor size was suppressed by administration of paclitaxel. Type IV means that chemosensitivity to the anticancer agent was low, wherein the tumor size continued to be increased even by administration of paclitaxel. As a result of the observation of the tumor size, as shown in Table 1, the cell A was classified into Type I, the cells B and C were classified into Type II, the cell D was classified into Type III, and the cell E was classified into Type IV. The classification results are shown in the column of "Effect of therapy" in Table 1.

(3) Measurement of CDK1 Specific Activity, CDK2 Specific Activity, and Expression Level of p21, and Setting of Threshold Values Activity and expression level of CDK1 and CDK2 respectively were measured with respect to the specimens obtained in the experiment (1) in accordance with the aforementioned measurement method, and the specific activity of CDK1 and the specific activity of CDK2 in the specimens were calculated. Also, the expression level of p21 in the specimens was measured in accordance with the aforementioned measurement method. The measurement results are shown in Table 1.

Threshold values were set based on the measurement results so that prediction could be made with a highest correct probability for the classification results in the experiment (2). Specifically, the threshold value for the CDK2 specific activity can be set in the range of 341.3 to 407.1. In this example, the threshold value for the CDK2 specific activity was set to 400. Also, the threshold value for the expression level of p21 can be set in the range of 8.77 to 10.96. In this example, the threshold value for the expression level of p21 was set to 10. Likewise, the threshold value for the CDK1 specific activity can be set in the range of 10.76 to 10.83. In this example, the threshold value for the CDK1 specific activity was set to 10.8. In Table 1, if a value is smaller than the threshold value, the value is indicted "Low", and if a value is larger than the threshold value value, the value is indicated "High".

that the group which is predicted to have a particularly high chemotherapeutic effectiveness could be accurately sorted out from the mice No. 1 to 46 by using the comparison result.

In the case where prediction was made based merely on a comparison result between expression level of p21 and its threshold value in Table 1, the cells belonging to Type IV could be predicted as Type IV with probability of 100%. This shows that the group which is predicted to have a particularly low chemotherapeutic effectiveness could be accurately sorted out from the mice No. 1 to 46 by using the comparison result.

TABLE 1

| mouse No. | Cell | Therapy using anticancer agent Effect of therapy | Specific activity of CDK2 Ts 400 | | Expression level of p21 Ts 10 | | Specifc activity of CDK1 Ts 10.8 | | Prediction Result | C/I |
|---|---|---|---|---|---|---|---|---|---|---|
| 1 | A | Type I | 407.1 | High | 0.00 | Low | 16.12 | High | Type I | C |
| 2 | A | Type I | 574.5 | High | 0.86 | Low | 16.82 | High | Type I | C |
| 3 | A | Type I | 545.0 | High | 1.26 | Low | 13.55 | High | Type I | C |
| 4 | A | Type I | 734.6 | High | 1.43 | Low | 11.79 | High | Type I | C |
| 5 | A | Type I | 634.1 | High | 1.34 | Low | 10.83 | High | Type I | C |
| 6 | A | Type I | 1083.2 | High | 1.93 | Low | 17.50 | High | Type I | C |
| 7 | A | Type I | 766.4 | High | 1.28 | Low | 21.77 | High | Type I | C |
| 8 | B | Type II | 156.2 | Low | 4.09 | Low | 27.00 | High | Type II | C |
| 9 | B | Type II | 192.8 | Low | 4.61 | Low | 31.56 | High | Type II | C |
| 10 | B | Type II | 109.1 | Low | 5.18 | Low | 20.53 | High | Type II | C |
| 11 | B | Type II | 328.6 | Low | 5.25 | Low | 13.39 | High | Type II | C |
| 12 | B | Type II | 64.8 | Low | 5.41 | Low | 33.32 | High | Type II | C |
| 13 | B | Type II | 130.5 | Low | 5.57 | Low | 32.01 | High | Type II | C |
| 14 | B | Type II | 171.6 | Low | 5.33 | Low | 34.33 | High | Type II | C |
| 15 | B | Type II | 140.3 | Low | 5.00 | Low | 34.21 | High | Type II | C |
| 16 | B | Type II | 157.9 | Low | 3.42 | Low | 35.27 | High | Type II | C |
| 17 | B | Type II | 92.1 | Low | 4.33 | Low | 25.40 | High | Type II | C |
| 18 | B | Type II | 41.9 | Low | 5.43 | Low | 13.90 | High | Type II | C |
| 19 | C | Type II | 163.6 | Low | 1.06 | Low | 25.48 | High | Type II | C |
| 20 | C | Type II | 213.3 | Low | 1.44 | Low | 11.25 | High | Type II | C |
| 21 | C | Type II | 209.9 | Low | 0.00 | Low | 22.64 | High | Type II | C |
| 22 | C | Type II | 341.2 | Low | 0.00 | Low | 39.14 | High | Type II | C |
| 23 | C | Type II | 106.9 | Low | 0.00 | Low | 21.35 | High | Type II | C |
| 24 | C | Type II | 206.6 | Low | 0.00 | Low | 11.22 | High | Type II | C |
| 25 | C | Type II | 140.6 | Low | 1.31 | Low | 13.77 | High | Type II | C |
| 26 | C | Type II | 98.6 | Low | 0.85 | Low | 7.06 | Low | Type III | I |
| 27 | C | Type II | 114.8 | Low | 0.00 | Low | 16.60 | High | Type II | C |
| 28 | C | Type II | 201.8 | Low | 0.00 | Low | 11.60 | High | Type II | C |
| 29 | C | Type II | 129.9 | Low | 0.77 | Low | 15.29 | High | Type II | C |
| 30 | C | Type II | 151.0 | Low | 0.00 | Low | 12.58 | High | Type II | C |
| 31 | C | Type II | 138.8 | Low | 0.64 | Low | 41.80 | High | Type II | C |
| 32 | C | Type II | 187.9 | Low | 0.57 | Low | 60.36 | High | Type II | C |
| 33 | C | Type II | 124.6 | Low | 0.53 | Low | 36.09 | High | Type II | C |
| 34 | C | Type II | 136.6 | Low | 0.29 | Low | 30.85 | High | Type II | C |
| 35 | D | Type III | 0.0 | Low | 8.76 | Low | 10.75 | Low | Type III | C |
| 36 | D | Type III | 80.1 | Low | 7.21 | Low | 0.00 | Low | Type III | C |
| 37 | D | Type III | 23.6 | Low | 7.62 | Low | 7.10 | Low | Type III | C |
| 38 | D | Type III | 0.0 | Low | 7.34 | Low | 6.48 | Low | Type III | C |
| 39 | D | Type III | 0.0 | Low | 6.39 | Low | 22.16 | High | Type II | I |
| 40 | D | Type III | 0.0 | Low | 5.40 | Low | 9.68 | Low | Type III | C |
| 41 | D | Type III | 71.6 | Low | 0.74 | Low | 10.04 | Low | Type III | C |
| 42 | E | Type IV | 55.7 | Low | 34.45 | High | 9.81 | Low | Type IV | C |
| 43 | E | Type IV | 50.2 | Low | 10.96 | High | 2.45 | Low | Type IV | C |
| 44 | E | Type IV | 59.1 | Low | 15.33 | High | 8.76 | Low | Type IV | C |
| 45 | E | Type IV | 0.0 | Low | 17.25 | High | 7.92 | Low | Type IV | C |
| 46 | E | Type IV | 56.4 | Low | 15.25 | High | 8.29 | Low | Type IV | C |

Ts: threshold value
C: correct
I: incorrect (4) Prediction

In the case where prediction was made based merely on a comparison result between CDK2 specific activity and its threshold value in Table 1, the cells belonging to Type I could be predicted as Type I with probability of 100%. This shows In the case where prediction was made based merely on a comparison result between CDK1 specific activity and its threshold value in Table 1, the mice No. 1 to 46 could be classified into the group belonging to Type I and Type II, and the group belonging to Type III and Type IV with probability of 96%. This shows that the mice No. 1 to 46 could be classified into a group which is predicted to have a relatively high chemotherapeutic effectiveness, and another group which is predicted to have a relatively low chemotherapeutic effectiveness, with high probability, by using the comparison result.

Thus, use of one of the comparison result between CDK2 specific activity and its threshold value, the comparison result between expression level of p21 and its threshold value, and the comparison result between CDK1 specific activity and its threshold value enables to predict the chemotherapeutic effectiveness against target tumor cells with high probability.

In the case where prediction was made based on a combination of the comparison result between CDK2 specific activity and its threshold value, and the comparison result between expression level of p21 and its threshold value in Table 1, the mice No. 1 to 46 could be classified into three groups: the group belonging to Type I; the group belonging to Type II and Type III, and the group belonging to Type IV, with probability of 100%.

In the case where prediction was made based on a combination of the comparison result between CDK2 specific activity and its threshold value, and the comparison result between CDK1 specific activity and its threshold value in Table 1, the group belonging to Type I could be sorted out with probability of 100%, the group belonging to Type II could be sorted out with probability of 96%, and the group belonging to Type III and Type IV could be sorted out with probability of 92% from the mice No. 1 to 46. In this case, the correct probability was 96% with respect to the total of the prediction results.

In the case where prediction was made based on a combination of the comparison result between expression level of p21 and its threshold value, and the comparison result between CDK1 specific activity and its threshold value in Table 1, the group belonging to Type I and Type II could be sorted out with probability of 96%, the group belonging to Type III could be sorted out with probability of 86%, and the group belonging to Type IV could be sorted out with probability of 100% from the mice No. 1 to 46. In this case, the correct probability was 96% with respect to the total of the prediction results.

Thus, use of the two comparison results among the comparison result between CDK2 specific activity and its threshold value, the comparison result between expression level of p21 and its threshold value, and the comparison result between CDK1 specific activity and its threshold value enables to classify the mice into three groups having different chemotherapeutic effectiveness with high probability, thereby enabling to predict the chemotherapeutic effectiveness against the target tumor cells.

In the case where prediction was made based on a combination of the comparison result between CDK2 specific activity and its threshold value, the comparison result between expression level of p21 and its threshold value, and the comparison result between CDK1 specific activity and its threshold value in Table 1, the group belonging to Type I could be sorted out with probability of 100%, the group belonging to Type II could be sorted out with probability of 96%, the group belonging to Type III could be sorted out with probability. of 86%, and the group belonging to Type IV could be sorted out with probability of 100% from the mice No. 1 to 46. In this case, the correct probability was 96% with respect to the total of the prediction results.

Thus, use of all the comparison results in Table 1 enables to classify the mice into four groups having different chemotherapeutic effectiveness with high probability, thereby enabling to predict the chemotherapeutic effectiveness against the target tumor cells.

The matching (correct prediction) and the non-matching (incorrect prediction) between the prediction results and the actual results by administration of the anticancer agent are shown in Table 2.

TABLE 2

| Sensitivity | Type | correct | incorrect |
| --- | --- | --- | --- |
| High | I | 7/7 | 0/7 |
| Medium | II | 26/27 | 1/27 |
| Slightly low | III | 6/7 | 1/7 |
| Low | IV | 5/5 | 0/5 |

Example 2

Figure 3:
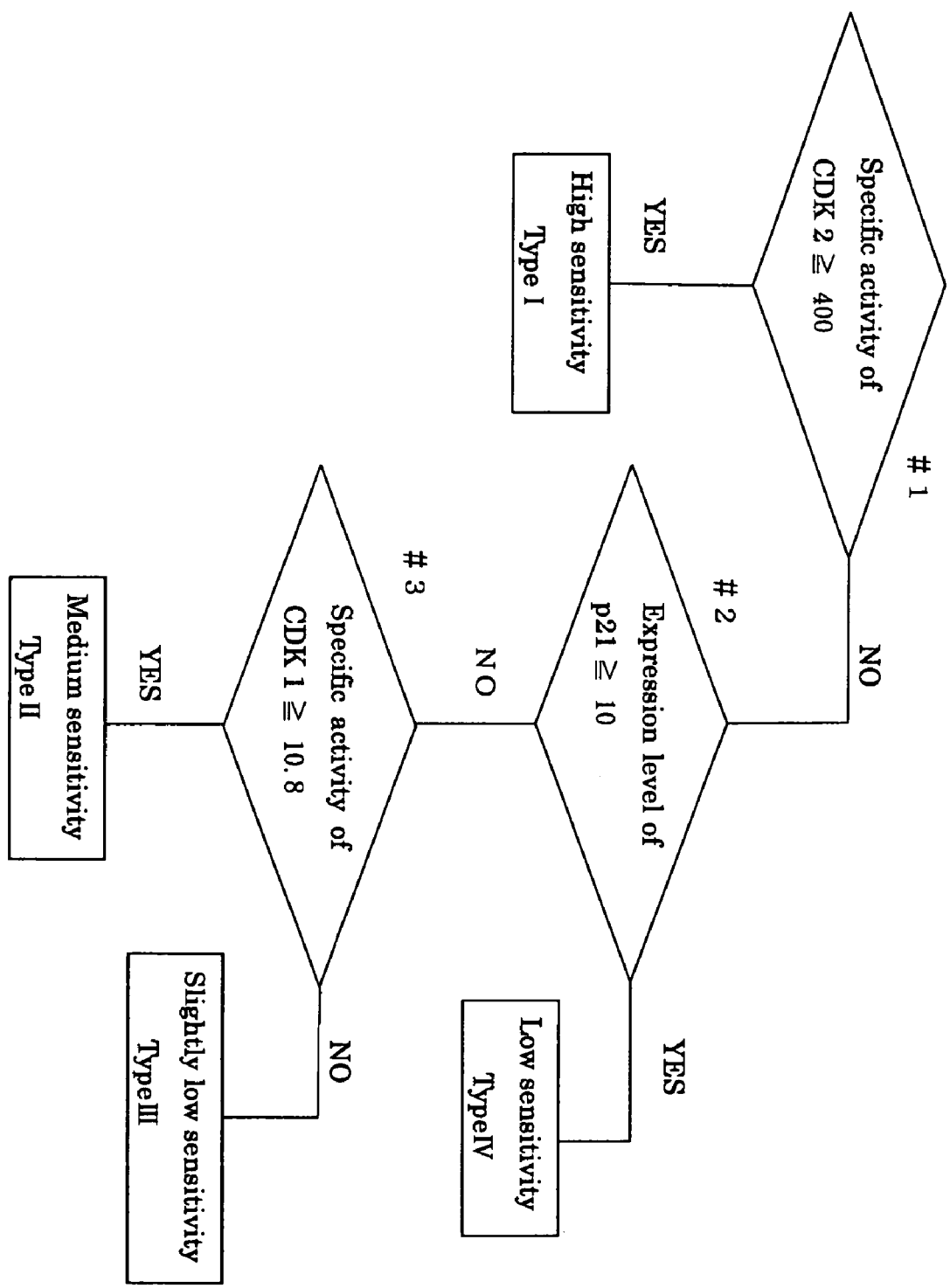
FIG. 3 is a flowchart showing operations of prediction adopted in the predicting method in Example 2.

Relation between Chemotherapeutic Effectiveness and Prediction Using Mouse Heterograft Based on the Decision Tree Prediction on chemosensitivity of the mouse heterograft to paclitaxel was made in accordance with the flowchart shown in FIG. 3, based on the comparison result between measured CDK2 specific activity and its threshold value, the comparison result between measured expression level of p21 and its threshold value, and the comparison result between measured CDK1 specific activity and its threshold value. Referring to FIG. 3, the measured CDK2 specific activity and its threshold value i.e. 400 was compared for the respective specimens in Step #1. The specimen having the CDK2 specific activity of 400 or more was predicted Type I. As for the specimen having the CDK2 specific activity smaller than 400, the measured expression level of p21 of the specimen was compared with its threshold value i.e. 10 (Step #2), because the chemotherapeutic effectiveness for the specimen could not be predicted in Step #1. The specimen whose expression level of p21 was 10 or more was predicted Type IV. Then, in Step #3, the measured CDK1 specific activity was compared with its threshold value i.e. 10.8 for the specimen in which the chemotherapeutic effectiveness could not be predicted in Step #2 because the expression level of p21 of the specimen was smaller than 10. The specimen whose CDK1 specific activity was not smaller than 10.8 was predicted Type II, and the specimen whose CDK1 specific activity was smaller than 10.8 was predicted Type III. In this way, prediction was made for all the specimens.

The aforementioned prediction results were compared with the classification results in the experiment (2) of Example 1. As a result of the comparison, the comparison result which showed matching was classified "correct", and the comparison result which showed non-matching was classified "incorrect". The prediction results, and the results on matching/non-matching between the classification results and the prediction results are shown in the column of "prediction" in Table 1. The prediction results in Example 2 were substantially the same as the prediction results in Example 1 with respect to all the specimens. Also, it was confirmed that the same results were obtained by changing the order of comparing steps in the flowchart shown in FIG. 3.

The correct probability in Example 2 was 96% based on the results in Tables 1 and 2. Thus, it is concluded that the prediction in Example 2 has a higher correct probability than the conventional prediction method. Further, the correct probability of 100% was obtained for the prediction results on Type I having a high chemosensitivity and Type IV having a low chemosensitivity.

Accordingly, the inventive predicting method enables to predict the chemotherapeutic effectiveness with probability as high as about 100%, and enables to predict, with probability as high as 90% or more as to whether the tumor would become smaller, although substantial disappearance of the tumor by the anticancer agent therapy could not be expected. Such prediction may provide useful information for determining whether to extirpate the tumor after reducing the tumor size by administration of the anticancer agent.

According to the inventive method, the chemotherapeutic effectiveness can be predicted for individual cancer patients with high probability. Accordingly, the inventive method provides useful information in a clinical facility for determining whether to perform the chemotherapy using anticancer agent.

What is claimed is:

1. A method for predicting an effectiveness of chemotherapy using an anticancer agent, the method being embodied in a computer readable medium encoded with a computer program for performing the method and comprising steps of:
    comparing activity of a cyclin dependent kinase (first CDK) contained in a tumor cell with a threshold value, wherein the tumor cell is obtained from a living body having been administered with the anticancer agent at least once; and
    predicting an effectiveness of chemotherapy using the anticancer agent on the living body, based on a comparison result of the comparing step.

2. The method according to claim 1, wherein said parameter is expression level of said CDK inhibitor.

3. The method according to claim 2, wherein the predicting step is carried out by predicting whether or not the tumor cell is substantially insensitive to the anticancer agent.

4. The method according to claim 1, wherein the predicting step is carried out by predicting whether or not the tumor cell is highly sensitive to the anticancer agent, based on a comparison result of the comparing step.

5. The method according to claim 1, further comprising a step of second comparing expression level of a cyclin dependent kinase inhibitor (CDK inhibitor) with a second threshold value, wherein,
    the predicting step being carried out by predicting the effectiveness based on comparison results of said first comparing step and said second comparing step.

6. The method according to claim 1, wherein the CDK is CDK1 or CDK2.

7. The method according to claim 1, wherein the ratio of activity versus expression level is a specific activity.

8. The method according to claim 1, wherein the anticancer agent is an anticancer agent sensitive against cells in M-phase.

9. The method according to claim 8, wherein the anticancer agent is a taxane anticancer agent.

10. The method according to claim 1, wherein the tumor cell is obtained from a living body upon lapse of ten to thirty hours after administration of the anticancer agent.

11. The method according to claim 5, wherein the CDK inhibitor is p21.

12. The method according to claim 5, wherein said predicting step is carried out by predicting which class of three chemosensitivity groups the tumor cell belongs to, based on comparison results of said first and second comparing steps.

13. The method according to claim 5, further comprising a step of third comparing ratio of activity versus expression level of a second CDK with a third threshold value, wherein said second CDK is different from said first CDK, and wherein the predicting step is carried out by predicting the effectiveness based on comparison results of said first, second and third comparing steps.

14. The method according to claim 13, wherein said predicting step is carried out by predicting which class of four chemosensitivity groups the tumor cell belongs to, based on comparison results of said first, second, and third comparing steps.

15. The method according to claim 14, wherein said first parameter is the ratio of activity versus expression level of said first CDK, said second parameter is the expression level of said CDK inhibitor, and said third parameter is the ratio of activity versus expression level of said second CDK.

16. A method for predicting an effectiveness of chemotherapy using an anticancer agent, the method being embodied in a computer readable medium encoded with a computer program for performing the method and comprising steps of:
    first comparing activity of a first cyclin dependent kinase (first CDK) contained in a tumor cell with a first threshold value, wherein the tumor cell is obtained from a living body having been administered with the anticancer agent at least once; and
    first predicting the effectiveness of chemotherapy using the anticancer agent on the living body, based on a comparison result of said first comparing step;
    if required, the method further comprising steps of:
    second comparing expression level of a cyclin dependent kinase inhibitor (CDK inhibitor) with a second threshold value; and
    second predicting the effectiveness of chemotherapy using the anticancer agent on the living body, based on a comparison result of said second comparing step.

17. The method according to claim 16, wherein said first CDK is CDK2 and said second CDK is CDK1.

18. The method according to claim 17, if required, further comprising steps of:
    third comparing ratio of activity versus expression level of a second CDK with a third threshold value, wherein said second CDK is different from said first CDK; and
    third predicting the effectiveness of chemotherapy using the anticancer agent on the living body, based on a comparison result of said third comparing step.

19. A method for predicting an effectiveness of chemotherapy using an anticancer agent, the method being embodied in a computer readable medium encoded with a computer program for performing the method and comprising steps of:
    first predicting the effectiveness of chemotherapy using the anticancer agent on a living body, based on a comparison of activity of a first cyclin dependent kinase (first CDK) contained in a tumor cell with a first threshold value, wherein the tumor cell is obtained from the living body having been administered with the anticancer agent at least once;
    if required, the method further comprising a step of second predicting the effectiveness, based on a comparison of expression level of a cyclin dependent kinase inhibitor (CDK inhibitor) with a second threshold value; and
    if required, the method further comprising a step of third predicting the effectiveness, based on a comparison of ratio of activity versus expression level of a second CDK with a third threshold value, wherein said second CDK is different from said first CDK.

* * * * *